United States Patent
Kotian (10) Patent No.: US 11,266,360 B2
(45) Date of Patent: Mar. 8, 2022

(54) METHODS AND SYSTEMS FOR COLLISION AVOIDANCE IN AN IMAGING SYSTEM

(71) Applicant: GE Precision Healthcare LLC, Milwaukee, WI (US)

(72) Inventor: Francois Kotian, Villepreux (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 168 days.

(21) Appl. No.: 16/777,118

(22) Filed: Jan. 30, 2020

(65) Prior Publication Data
US 2021/0236069 A1    Aug. 5, 2021

(51) Int. Cl.
*A61B 6/00*    (2006.01)
*A61B 6/10*    (2006.01)
*G01S 15/08*    (2006.01)

(52) U.S. Cl.
CPC .............. *A61B 6/102* (2013.01); *A61B 6/547* (2013.01); *G01S 15/08* (2013.01); *A61B 6/4405* (2013.01); *A61B 6/4441* (2013.01)

(58) Field of Classification Search
CPC ................................ A61B 6/547; A61B 6/102
See application file for complete search history.

(56) References Cited

U.S. PATENT DOCUMENTS

| | | | |
|---|---|---|---|
| 2009/0232282 A1* | 9/2009 | Belson | A61B 6/107 378/203 |
| 2018/0289342 A1* | 10/2018 | Chandwadkar | A61B 5/6802 |
| 2020/0205753 A1* | 7/2020 | Yifat | A61B 6/107 |

OTHER PUBLICATIONS

"Philips Allure Video HD," YouTube Website, Available Online at https://www.youtube.com/watch?v=WcDVnKwe1lw, Aug. 26, 2014, 3 pages.

* cited by examiner

*Primary Examiner* — Dani Fox (57) ABSTRACT

Various systems are provided for collision avoidance in an x-ray imaging system. In one example, an x-ray system includes a moveable arm comprising an x-ray source arranged at a first end and an x-ray detector arranged at a second end, an ultrasonic sensor positioned on the movable arm, the x-ray source, or the x-ray detector, and a sterile drape configured to be positioned over at least a portion of the movable arm, the x-ray source, and/or the x-ray detector, the sterile drape including an adhesive pad configured to contact a front face of the ultrasonic sensor.

12 Claims, 6 Drawing Sheets

METHODS AND SYSTEMS FOR COLLISION AVOIDANCE IN AN IMAGING SYSTEM

TECHNICAL FIELD

Embodiments of the subject matter disclosed herein relate to collision avoidance in an imaging system, such as an x-ray imaging system.

DISCUSSION OF ART

It is frequently desired to conduct an x-ray examination of a patient from several different positions and is often preferable to do so without the need to reposition the patient. C-arm x-ray imaging systems have been developed to meet these needs and are now well-known in the medical and surgical arts. The C-arm x-ray imaging system is especially useful in that it is small enough and mobile enough to be present in an operating or exam situation without requiring the physician to repeatedly move or requiring the patient to change positions to obtain a suitable image.

The term "C-arm" refers to the generally C-shaped gantry of the machine, to which an x-ray source and an x-ray detector are mounted on opposing ends of the C-arm such that x-rays emitted by the x-ray source are incident on and detected by the x-ray detector. The x-ray source and x-ray detector are positioned such that when, for example, a human extremity is interposed between the x-ray source and the x-ray detector and irradiated with x-rays, the x-ray detector produces data representative of characteristics of the interposed object. The data produced is typically displayed on a monitor and electronically stored.

BRIEF DESCRIPTION

In one embodiment, an x-ray system includes a moveable arm comprising an x-ray source arranged at a first end and an x-ray detector arranged at a second end, an ultrasonic sensor positioned on the movable arm, the x-ray source, or the x-ray detector, and a sterile drape configured to be positioned over at least a portion of the movable arm, the x-ray source, and/or the x-ray detector, the sterile drape including an adhesive pad configured to contact a front face of the ultrasonic sensor.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Collision management is a major issue in some medical imaging systems, such as interventional x-ray systems (also referred to herein as C-arm imaging systems). Parts of the imaging system in motion (gantry and table) shall not hurt patients and medical staff, and shall not damage or be damaged as a result of collisions. Strategies including model-based and sensor based collision management may be used. Model-based collision management relies on a priori knowledge of patient position and size to prevent collisions. Additionally the geometry and location of all x-ray system parts may be known, including table and gantry. In particular, the x-y-z and orientation position of the table top are known reasonably precisely and combined with the a priori patient geometry model. The model-based collision management is an approximation and does not address medical staff and ancillary equipment, any of which may move during a procedure. Switch-based sensors or pressure-based sensors may be used to stop motion in the event of a collision, but such strategies are reactive and cannot prevent initial collisions. Capacitive-type sensors may be used in components of the imaging system that are most likely to come into contact with the patient, in particular the detector of the imaging system (where the output from the capacitive sensors may be used in feedback control of the position of the detector to achieve a desired source-to-image distance), but efficient capacitive sensors are expensive. Thus, currently, the general strategy for collision avoidance in imaging systems is to limit speed, in particular in close proximity of where the patient is supposed to be, and always have motion under direct operator control. The current strategy may be slow and over-conservative or over-protective, thus frustrating operators/clinicians, delaying the time until images can be acquired, and/or causing other issues.

One approach for detecting and avoiding collision in an imaging system includes incorporating ultrasonic range sensors into various moving parts of the imaging system, such as on/near the imaging detector and on the supporting arm of the imaging system. Ultrasonic sensors are effective and inexpensive, and thus may allow possible collision targets to be identified before a collision occurs. However, parts of the interventional imaging system in proximity of the sterile field must be protected using sterile draping. If placed under sterile drapes, ultrasonic sensors are not directly usable because sterile drapes are detected as obstacles (e.g., the drapes reflect the sound waves from the ultrasonic sensors and occlude detection of objects beyond the drapes).

Thus, according to embodiments disclosed herein, the sterile draping may be maintained in tight contact with the surface(s) of the ultrasonic sensor(s) via adhesive, static cling, or another mechanism so that large variations in acoustic impedance and reflection are reduced or avoided. While some signal loss may occur and limit the range of the sensor, obstacles (e.g., the patient, medical staff) may be sensed through sterile drapes at a distance of centimeters to a few tenths of centimeters by the ultrasonic sensors. The sterile drapes may include embedded adhesive pads at the location of the ultrasonic sensors, where the adhesive pads include pressure-sensitive adhesive or regions of material having a high static cling.

Figure 1:
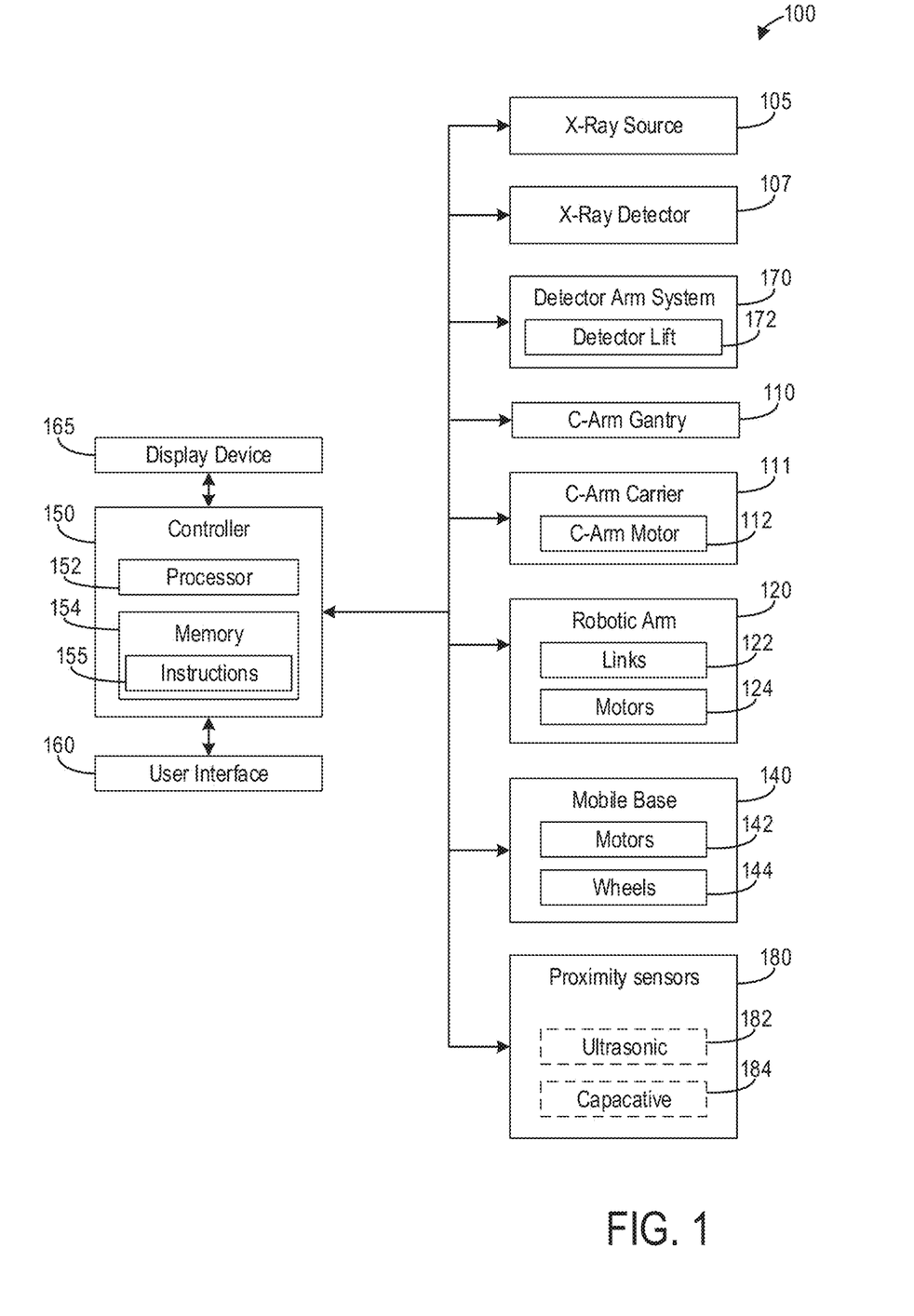
FIG. 1 is a block diagram of a medical imaging system, according to an embodiment.
Figure 2:
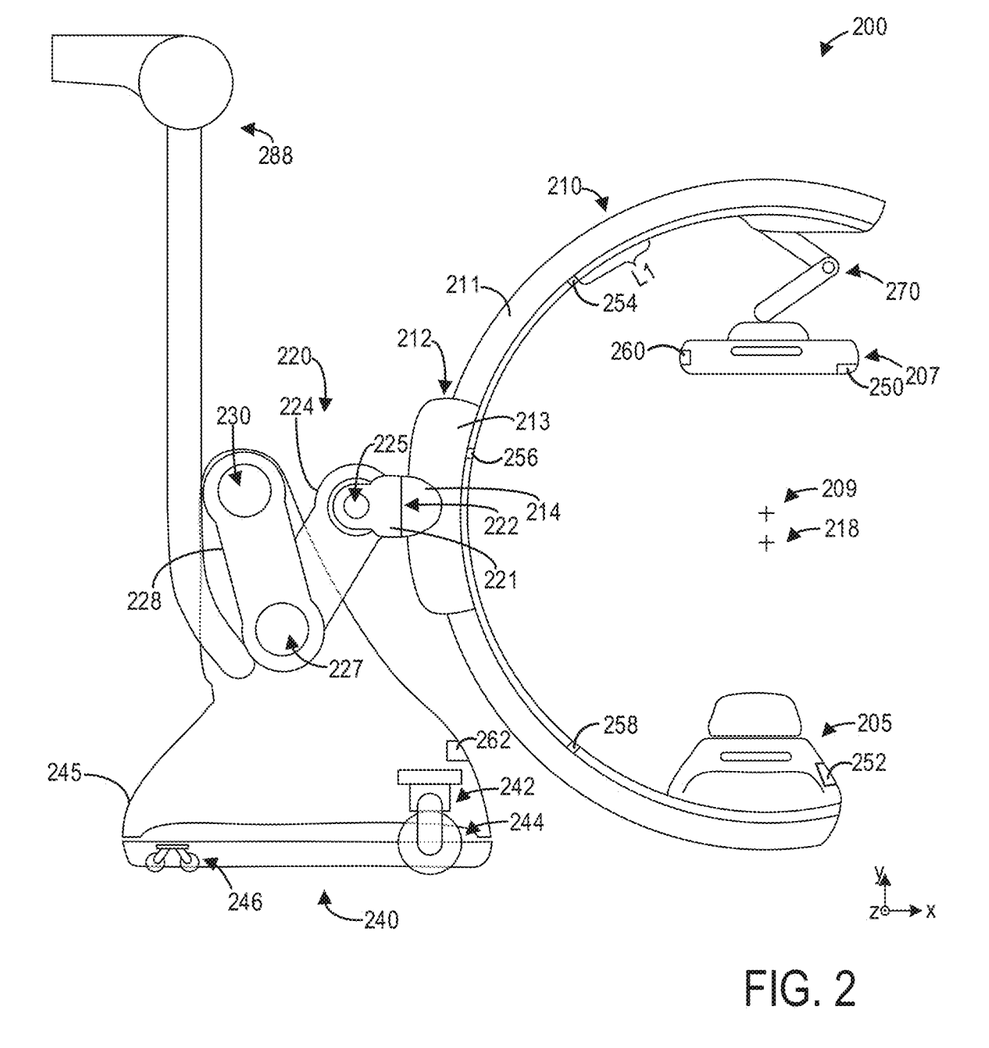
FIG. 2 is a side view of a medical imaging system including a C-arm and a plurality of ultrasonic proximity sensors, according to an embodiment.
Figure 3:
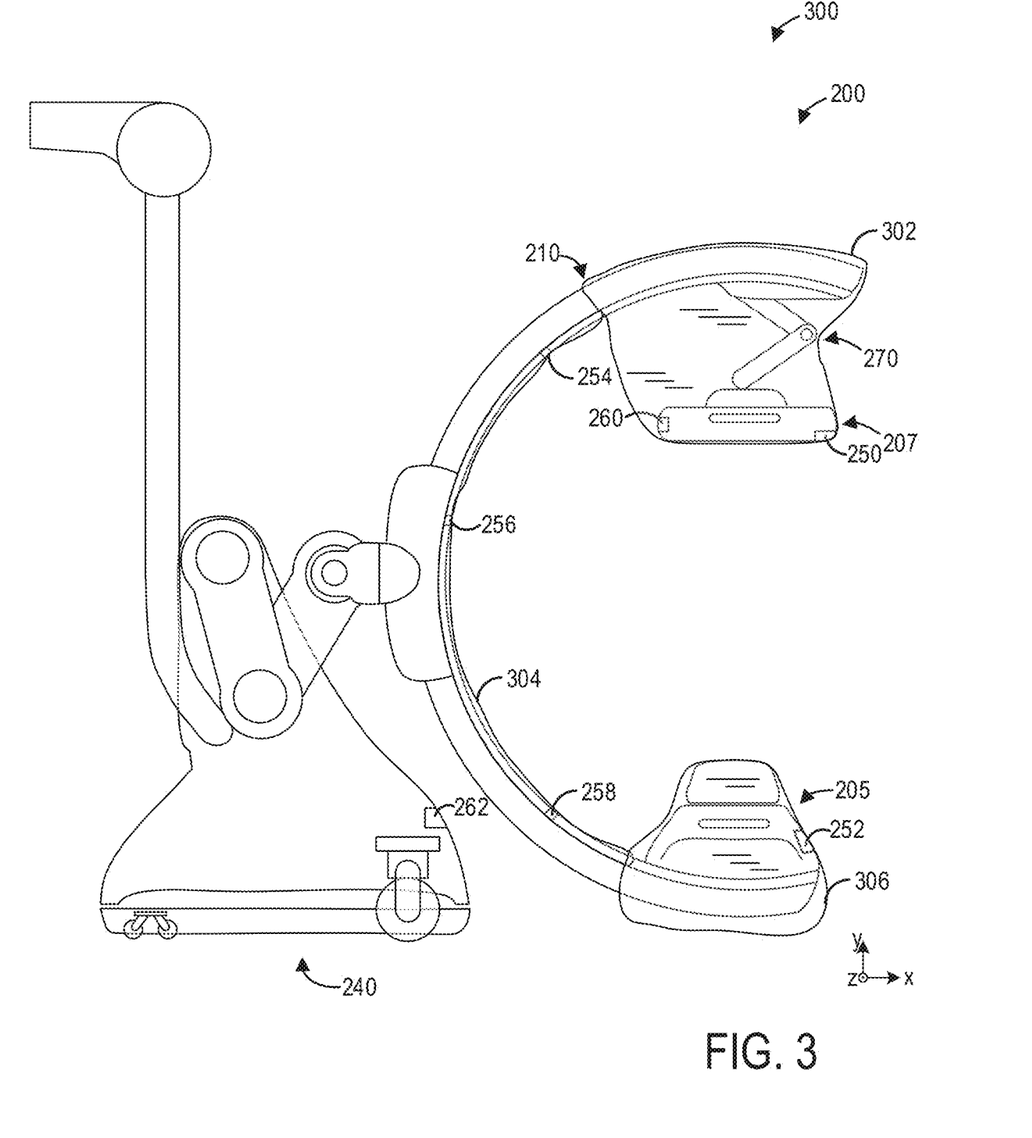
FIG. 3 is a side view of the medical imaging system of FIG. 2 including a plurality of sterile drapes positioned around components of the medical imaging system, the sterile drapes including adhesive pads configured to contact the plurality of ultrasonic sensors.
Figure 5:
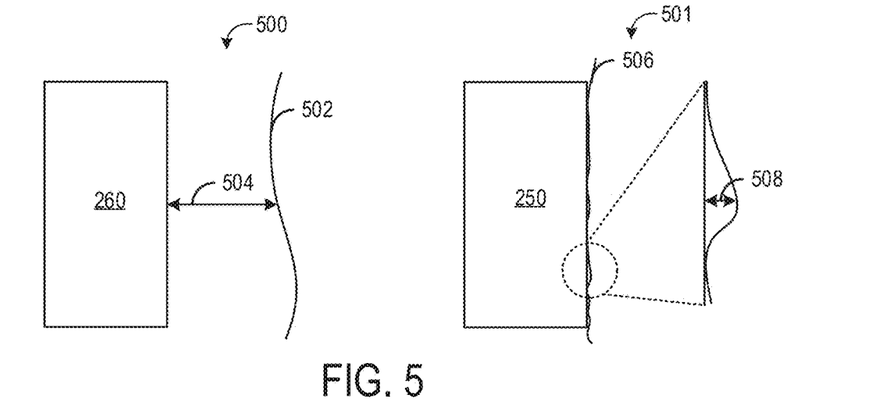
FIG. 5 shows magnified views of two proximity sensors positioned relative to a sterile drape, according to an embodiment.
Figure 6:
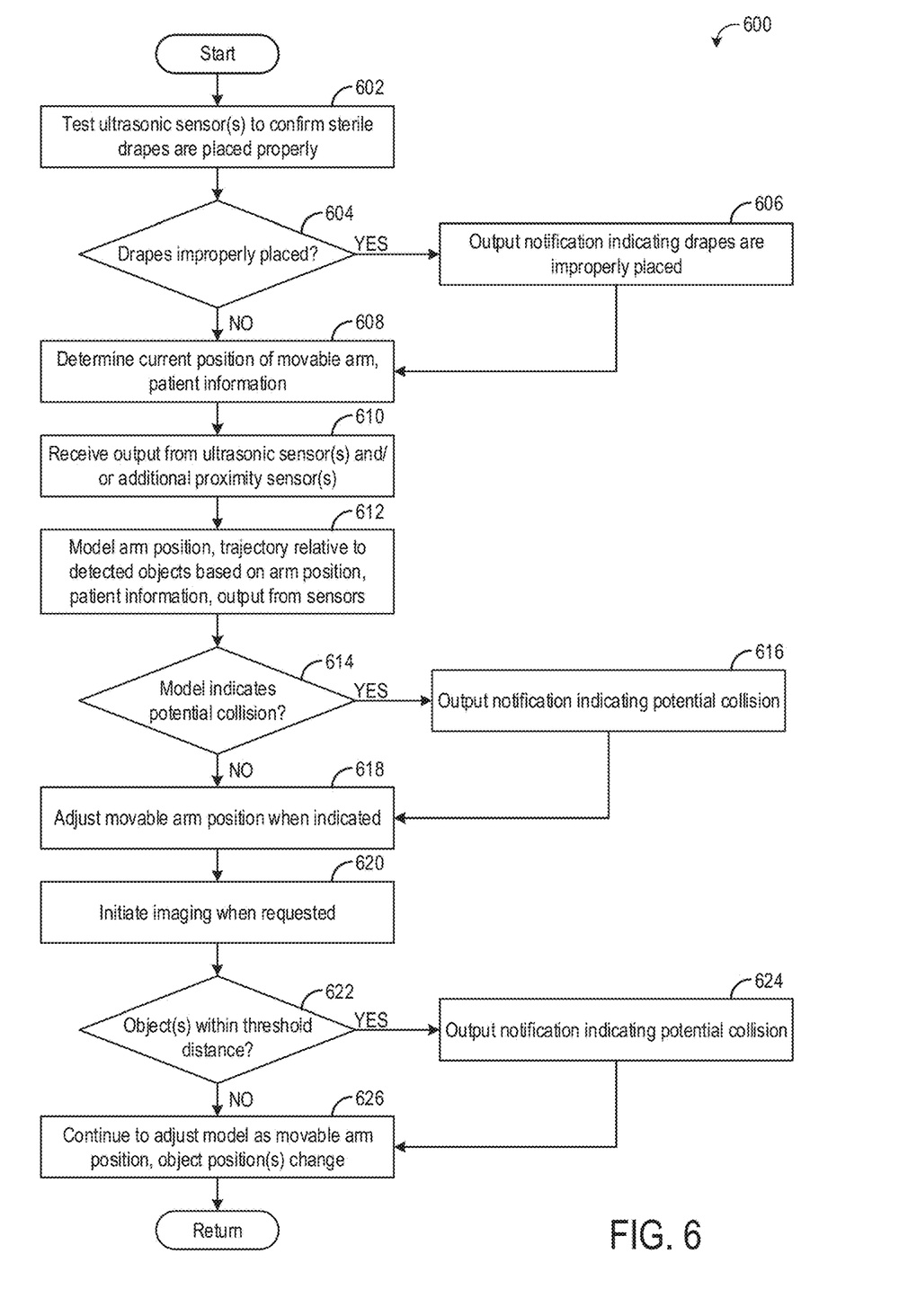
FIG. 6 is a flow chart illustrating a method for collision avoidance in a medical imaging system.

FIGS. 1 and 2 show an example imaging system having moving parts in which the collision avoidance system of the present disclosure may be incorporated, herein in the form of a C-arm x-ray imager. FIG. 3 shows an example set of sterile drapes positioned over the C-arm x-ray imager of FIG. 2, with the sterile drapes having adhesive pads at the locations where the sterile drapes would otherwise cover the ultrasonic sensors. These adhesive pads may facilitate contact between the ultrasonic sensors and the sterile drapes, as shown in FIG. 5. FIG. 34 shows an example sterile drape having a plurality of adhesive pads. FIG. 6 shows a method for collision avoidance in an x-ray imaging system based on output from one or more ultrasonic sensors.

FIGS. 2-5 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 shows a block diagram illustrating components of an example x-ray imaging system 100. The x-ray imaging system 100 comprises an x-ray source 105 and an x-ray detector 107 mounted on a C-arm gantry 110.

The detector arm system 170 includes a detector arm motor or detector lift 172 for adjusting the position of the x-ray detector 107. For example, the detector lift 172 may translate and/or rotate the x-ray detector 107 relative to the C-arm gantry 110.

The C-arm gantry 110 includes a C-arm motor 112 for adjusting the position of the C-arm gantry 110. More specifically, the C-arm gantry 110 is mechanically coupled to a C-arm carrier 111 which includes the C-arm motor 112, and the C-arm motor 112 may be driven to adjust the position of the C-arm gantry 110 with respect to the C-arm carrier 111, as described further herein with regard to FIG. 2.

The x-ray imaging system 100 further comprises a robotic arm 120 mechanically coupled to the C-arm gantry 110 via the C-arm carrier 111. The robotic arm 120 includes a plurality of links 122 and motors 124 positioned at joints between the links 122, as described further herein. In particular, the plurality of links 122 of the robotic arm 120 includes a first link coupled to the C-arm carrier 111 and thus forming a first motorized joint between the first link and the C-arm carrier 111 for adjusting a position of the C-arm carrier 111 relative to the first link, a second link coupled to the first link and thus forming a second motorized joint between the first link and the second link for adjusting a position of the first link relative to the second link, and a third link coupled to the second link and thus forming a third motorized joint between the second link and the third link for adjusting a position of the second link relative to the third link. Furthermore, the third link is mechanically coupled to a base 140, thus forming a fourth motorized joint between the third link and the base 140 for adjusting a position of the third link relative to the base 140.

The base 140 may include one or more motors 142 for driving one or more wheels 144 to adjust a position of the base 140. In addition, one or more of the wheels 144 may be free or un-motorized, as described further herein. For example, the wheels 144 may comprise two motorized wheels (with two motors 142 per motorized wheel) and one non-motorized wheel. In some examples, base 140 may be fixed in position and not configured to move, and thus the wheels and motors driving the wheels may be omitted.

The x-ray imaging system 100 further includes a controller 150 comprising a processor 152 and a non-transitory memory 154. A method for controlling the x-ray imaging system 100 may be stored as executable instructions 155 in the non-transitory memory 154 and executed by the processor 152. An example method that may be implemented as the instructions 155 is described further herein with regard to FIG. 6.

The x-ray imaging system 100 further include a user interface 160 for receiving input from a user or operator of the x-ray imaging system 100. The user interface 160 may be communicatively coupled to the controller 150 for providing commands input by a user via the user interface 160 to the controller 150. The user interface 160 may comprise one or more of a keyboard, a mouse, a trackball, one or more knobs, one or more joysticks, a touchpad, a touchscreen, one or more hard and/or soft buttons, a smartphone, a microphone, a virtual reality apparatus, and so on. The user interface 160 may thus enable voice control, and display of information such as simulated motion or possible collisions using the virtual reality apparatus or an interactive display device (e.g., touchscreen). In some examples the user interface 160 may be remotely located relative to the x-ray imaging system 100. For example, the user interface 160 may be communicatively coupled to the controller 150 and/or the x-ray imaging system 100 via a wired or wireless connection, and may be positioned away from the base 140.

As discussed further herein, a user of the mobile x-ray imaging system 100 may input a desired isocenter position via the user interface 160, for example. The controller 150 may then determine position adjustments to one or more of the detector arm system 170, the C-arm gantry 110, the robotic arm 120, and the mobile base 140 to align an isocenter of the mobile x-ray imaging system 100 with the desired isocenter position. As another example, a user of the mobile x-ray imaging system 100 may directly control the position of one or more components of the mobile x-ray imaging system 100 relative to other components of the mobile x-ray imaging system 100 via the user interface 160. For example, the user may directly input, via a joystick or knob, for example, position adjustments to one or more components of the mobile x-ray imaging system 100. As another example, the motion of the components of the mobile x-ray imaging system 100 may be pre-programmed such that the user does not directly control any movement, but instead initiates the start of the pre-programmed motion. The motion may comprise complex motions, with continuous motion of the isocenter.

The controller 150 is further communicatively coupled to a display device 165 for displaying one or more x-ray images acquired via the x-ray detector 107. Further, in some examples, one or more of the controller 150, the user interface 160, and the display device 165 may be positioned away from (e.g., remotely from) the remaining components of the x-ray imaging system 100.

The x-ray imaging system 100 includes a collision avoidance system configured to detect objects (e.g., people, tables, medical equipment) in proximity to various components of the x-ray imaging system 100. The collision avoidance system includes a proximity sensors 180, which may include a plurality of ultrasonic sensors 182 and/or one or more capacitive sensors 184.

Each sensor of the plurality of ultrasonic sensors may generate pulses of ultrasonic signals, and may receive reflected ultrasonic signals (e.g., echoes, where the transmitted ultrasonic signals are reflected off of objects in proximity and return back to the ultrasonic sensor). Based on the amount of time from when an ultrasonic pulse is transmitted from the ultrasonic sensor to when a reflected ultrasonic signal is received at the ultrasonic sensor, a distance of an object from the ultrasonic sensor may be determined. Each proximity sensor may be configured to send proximity information to the controller 150, and the controller 150 may be configured to output alerts based on the proximity information, update model-based collision avoidance routines based on the proximity information, etc., as will be explained in more detail below.

FIG. 2 shows a schematic illustration of an example x-ray imaging system 200. The x-ray imaging system 200 includes the components depicted in FIG. 1. For example, the x-ray imaging system 200 includes an x-ray source 205 and an x-ray detector 207 mounted on a C-arm gantry 210. The C-arm gantry 210 is coupled to a base 240 of the mobile x-ray imaging system 200 via a C-arm carrier 212 and a robotic arm 220. The C-arm carrier 212 and the robotic arm 220 may be controlled to adjust a position of an imaging isocenter 209, also referred to herein simply as isocenter 209, relative to the base 240, to adjust a position of the C-arm gantry 210 relative to the base 240, and/or to adjust a position of the x-ray source 205 and the x-ray detector 207 relative to the isocenter 209.

To be specific, the isocenter 209 of the C-arm gantry 210 comprises the intersection of the optical axis (defined by the focus of the x-ray source 205 and the center of the x-ray detector 207 or the normal to the x-ray detector 207 that goes through the focus) and the C-arm rotation axis along the carrier 212. In some examples, the first link 221 is rotated at the second joint 225 relative to the second link 224 such that the first link 221 is always aligned to the isocenter. However, it should be appreciated that in other examples, the first link 221 may not be aligned with the isocenter.

The C-arm carrier 212 comprises a carrier base 213 coupled to the C-arm gantry 210 and configured to rotate the C-arm gantry 210 along a gantry track 211 in the depicted x-y plane. To that end, the carrier base 213 may include one or more motors (not shown), such as the C-arm motor 112, for sliding the C-arm gantry 210 along the gantry track 211. The C-arm gantry 210 may be rotated in the x-y plane about a rotation axis or the isocenter 209 relative to the C-arm carrier 212, such that the x-ray source 205 and the x-ray detector 207 are rotated relative to the isocenter 209 in the x-y plane.

In addition, the C-arm carrier 212 further comprises a support base 214 mechanically coupled to the carrier base 213 as depicted. The support base 214 is in turn mechanically coupled to a first link 221 of the robotic arm 220, thereby forming a first joint 222 between the first link 221 and the C-arm carrier 212. A motor 124 of the robotic arm 220 is configured to rotate the C-arm carrier 212, and thus the C-arm gantry 210, relative to the first link 221 of the robotic arm 220 at the motorized first joint 222, such that the C-arm gantry 210 rotates in the depicted y-z plane. That is, the C-arm carrier 212 rotates at the first joint 222 relative to the first link 221 in the y-z plane. In this way, the carrier base 213 and the C-arm gantry 210 coupled thereto (as well as the components mounted to the C-arm gantry 210) may rotate in the y-z plane relative to the first link 221 of the robotic arm 220. Thus, the C-arm gantry 210 and the components mounted thereon may be rotated via the C-arm carrier 212 and the first joint 222 about the isocenter 209 in three-dimensional space (e.g., in the x-y plane via the C-arm carrier 212, and in the y-z plane via the first joint 222).

Further, the first link 221 of the robotic arm 220 is mechanically coupled to a second link 224 of the robotic arm 220 at a second joint 225. The robotic arm 220 includes a motor 124 (not pictured in FIG. 2) at the joint 225 for rotating the first link 221 relative to the second link 224. In particular, the first link 221 may be rotated about the second joint 225 in the depicted x-y plane. The second link 224 of the robotic arm 220 is mechanically coupled to a third link 228 of the robotic arm 220 via a third joint 227. The robotic arm 220 includes a motor 124 (not pictured in FIG. 2) at the third joint 227 for rotating the second link 224 in the x-y plane relative to the third link 228. Further, the third link 228 of the robotic arm 220 is mechanically coupled to the base 240 at a fourth joint 230. The robotic arm 220 includes a motor 124 (not pictured in FIG. 2) at the fourth joint 230 for rotating the third link 228 in the x-y plane relative to the mobile base 240.

Thus, the robotic arm 220 of the mobile x-ray imaging system 200 comprises a first link 221, a second link 224, and a third link 228, as well as a first joint 222, a second joint 225, a third joint 227, and a fourth joint 230. The first joint 222 provides a degree of freedom in the depicted y-z plane, while the second joint 225, the third joint 227, and the fourth joint 230 each provide a degree of freedom in the depicted x-y plane. Each joint is motorized to enable relative motion of the links of the robotic arm 220 relative to each other, as well as to the C-arm gantry 210 and the mobile base 240. By controlling the relative positions of each link, the position of the C-arm gantry 210 as well as the x-ray source 205 and the x-ray detector 207 mounted thereon are adjustable relative to the base 240 in three-dimensional space.

The x-ray imaging system 200 further includes a detector arm system 270 comprising one or more robotic arms configured to adjust a position of the x-ray detector 207. The detector arm system 270 may be controlled to increase or decrease the distance of the x-ray detector 207 from the C-arm gantry 210, thereby adjusting the position of the imaging center 218 of the mobile x-ray imaging system 200, which is located in the central point between the x-ray detector 207 and the x-ray source 205. The components of the x-ray imaging system 200 other than the detector arm system 270 may be controlled to adjust the position of the imaging center 218 in three-dimensional space. For example, controlling the robotic arm 220 enables a translation of the imaging center 218 in the depicted x-y plane. Furthermore, rotation of the C-arm gantry 210 at the first joint 222 in the y-z plane, as well as rotation of the C-arm gantry 210 relative to the C-arm carrier 212, adjusts the relative position of the x-ray source 205 and the x-ray detector 207 relative to the imaging center 218 in three-dimensional space.

The base 240 includes a plurality of wheels including driven wheels 244 and free wheels 246. The driven wheels 244 may be driven by one or more motors 242 for moving the base 240 and thus the entire x-ray imaging system 200. In addition to moving the x-ray imaging system 200 along the x-axis (i.e., to the left and right), the motor 242 may drive the driven wheels 244 in the z direction, thus enabling the x-ray imaging system 200 to be re-positioned in any orientation in the x-z plane. As an example, two motors 242 for each of the driven wheels 244 may be provided, wherein one motor 242 comprises a traction motor and a second motor 242 comprises a direction motor. In other examples, dual wheels (with differential traction motors), omnidirectional wheels, or other types of motorized wheels may be used. The free wheels 246 may not be driven by a motor. Further, as depicted, the driven wheels 244 may be positioned in the front of the mobile base 240 (i.e., on the side of the mobile base 240 closer to the C-arm gantry 210) and thus may be advantageously positioned closer to the center of gravity of the x-ray imaging system 200. In some examples, the free wheels 246 may be positioned at the front side of the base 240 on a structure extending towards the C-arm gantry 210. In some examples, all wheels of the mobile x-ray imaging system 200 may be driven wheels 244.

In some examples, the x-ray imaging system 200 may include a high voltage generator 274 housed within the housing 245 of the base 240. Providing the high voltage generator 274 within the base 240 increases the weight of the base 240, thus stabilizing the x-ray imaging system 200. Furthermore, providing the high voltage generator 274 within the base 240 eliminates the need to house the high voltage generator 274 remotely from the x-ray imaging system 200, thereby eliminating long high-voltage cables typically connected to the x-ray source 205 via the tether 288 for providing the x-ray source 205 with high voltages.

Further, a tether 288 may couple the x-ray imaging system 200 to a ceiling of the room wherein the mobile x-ray imaging system 200 is installed. Power, data, and cooling may be provided via the tether 288.

Further, in some examples, an on-board generator, a heat exchanger, and a battery may be provided at the base 240 to eliminate the tether 228 and thus enable fully autonomous operation of the x-ray imaging system 200.

The x-ray imaging system 200 includes a plurality of proximity sensors, including a first ultrasonic sensor 250, a second ultrasonic sensor 252, a third ultrasonic sensor 254, a fourth ultrasonic sensor 256, and a fifth ultrasonic sensor 258. As shown, first ultrasonic sensor 250 is positioned on the x-ray detector 207. Second ultrasonic sensor 252 is positioned on the x-ray source 205 (though other locations are possible, such as at a bottom of the C-arm proximate the x-ray source). The third ultrasonic sensor 254, fourth ultrasonic sensor 256, and fifth ultrasonic sensor 258 may each be positioned along an inner surface of the C-arm 210, between the x-ray detector 207 and the x-ray source 205. The collision avoidance system may include one or more additional proximity sensors, such as capacitive sensor 260 which is position on the x-ray detector 207 in the illustrated example. The additional proximity sensors may be capacitive-type and/or switch-type sensors. Other proximity sensors may be included on the x-ray imaging system without departing from the scope of this disclosure. Further, additional ultrasonic sensors, such as sixth ultrasonic sensor 262, may be positioned on the base 240 and/or other components of the x-ray imaging system 200.

Note that depending on the location of the proximity sensors, the proximity sensors may detect other parts of the x-ray imaging system within the sensing range of the proximity sensors. These can be filtered out based on time (distance). Similarly a specific pattern (e.g., combination of echoes from the whole set of ultrasonic sensors) may either be considered normal or abnormal depending on the geometry of the system (angles of the C-arm, position of the detector, position of the gantry vs the table, position of the table top, etc.).

The ultrasonic sensors described above may provide proximity sensing that may assist in reducing or avoiding collisions between the x-ray imaging system 200 and a patient or other objects in an exam room, such as medical equipment. The ultrasonic sensors may be inexpensive, which may facilitate incorporation of multiple ultrasonic sensors along the C-arm 210, at the x-ray source 205, at the x-ray detector 207, and/or at the base 240. However, the x-ray imaging system 200 is configured to be utilized during active surgical or other medical procedures, and thus various components of the x-ray imaging system 200 are typically covered in sterile draping when the x-ray imaging system 200 is in use. For example, before utilizing the x-ray imaging system 200 during an interventional procedure such as angioplasty, the C-arm 210, x-ray source 205, and x-ray detector 207 may each be covered in a sterile draping comprised of plastic or another medical grade material. The sterile draping may be positioned around the components of the x-ray imaging system, but may be draped so as to hang apart from the components, at least in some portions, by a few millimeters to even a few centimeters. The sterile draping may act as an obstacle to the ultrasonic signals emitted by the ultrasonic sensors, causing the ultrasonic signals emitted by the ultrasonic sensors to be reflected back to the ultrasonic sensors. As such, the sterile draping may be detected by the ultrasonic sensors as an object, which may prevent the ultrasonic sensors from being able to detect objects beyond the sterile draping, essentially making the ultrasonic sensors unusable for proximity detection and collision avoidance.

Thus, according to embodiments disclosed herein, the sterile draping may include adhesive pads including pressure-sensitive adhesive or static cling regions positioned to correspond to the locations of the ultrasonic sensors. When the sterile draping is positioned over the components of the x-ray imaging system 200, the sterile draping may be brought into contact with the outer surfaces of the ultrasonic sensors (e.g., the front/transducer face of the ultrasonic sensor). When the draping is flush/in contact with the front face/transducer of the ultrasonic sensor, the draping is no longer detected as an object. Rather, the ultrasonic signals may pass through the draping and may then be reflected off of any objects within a certain range of the ultrasonic sensor and return to the ultrasonic sensor.

FIG. 3 shows an example 300 of the x-ray imaging system 200 of FIG. 2 after the x-ray imaging system 200 has been draped in sterile drapes. As shown, the x-ray imaging system 200 has been draped in three drapes, a first drape 302, a second drape 304, and a third drape 306. The first drape 302 is positioned around the x-ray detector 207, the second drape 304 is positioned around at least the inner circumference of the C-arm 210 between the x-ray detector 207 and the x-ray source 205, and the third drape 306 is positioned around the x-ray source 205. As appreciated by FIG. 3, the drapes may be in face-sharing contact with each of the ultrasonic sensors. The drapes may be brought into and maintained in contact with the ultrasonic sensors due to adhesive pads on the drapes, as will be explained in more detail below with respect to FIG. 4. In other examples, the drapes may be brought into and maintained in contact with the ultrasonic sensors due to an air induction system that draws air around the ultrasonic sensors, thereby compelling the drapes to contact the ultrasonic sensors, and/or other mechanisms.

To cover the x-ray imaging system 200 in sterile draping, a user may first cover the C-arm 210 with the second drape 304. The second drape 304 may include three adhesive pads in the example shown in FIG. 3. As the user attaches the second drape 304 to the C-arm, the user may remove a backing covering a first adhesive pad, align the first adhesive pad to an ultrasonic sensor (e.g., third ultrasonic sensor 254), and press the adhesive pad onto the ultrasonic sensor. The user may repeat the process for the remaining adhesive pads/ultrasonic sensors. The second drape 304 may include a plurality of clips that may be positioned around the main body of the C-arm to maintain the second drape in position. The user may then position first drape 302 over the detector 207 and position third drape 306 over the x-ray source 205. For example, the first drape 302 may be shaped like a large bag, and thus may have an opening through which the detector 207 may be positioned into the first drape 302. The first drape 302 may include an adhesive pad at a positon corresponding to a position of an ultrasonic sensor (e.g., first ultrasonic sensor 250). The user may remove the backing on the adhesive pad before pulling the first drape 302 over the detector, align the adhesive pad with the ultrasonic sensor, and then press the adhesive pad onto the ultrasonic sensor. The first drape 302 may be held in place by an elastic band around a portion of the detector 207 or via another mechanism. The user may position the third drape 306 in a similar manner as the first drape 302.

Thus, the ultrasonic sensors may be brought into face-sharing contact with the sterile drapes. In contrast, the x-ray imaging system may include one or more other sensors that are not sensitive to the presence or absence of the sterile drapes, such as additional proximity sensor 260, the detector elements of the detector 207, etc. These other sensors may be separated from the drapes by a gap of any distance, and the sterile drapes may lack adhesive pads in locations corresponding to these sensors.

FIG. 5 shows magnified views of two proximity sensors that are covered by the first drape 302. A first view 500 shows the additional proximity sensor 130 and a first portion 502 of the first drape 302 that covers the additional proximity sensor 260, where the additional proximity sensor is not an ultrasonic sensor. As shown by the first view 500, the additional proximity sensor 260 is separated from the first portion 502 by a gap 504. The gap 504 may be relatively large, such as 1 cm or more. The first portion 502 may not include an adhesive pad.

A second view 501 shows the first ultrasonic sensor 250 and a second portion 506 of the first drape 302. The second portion 506 includes an adhesive pad and is shown in face-sharing contact with a front face of the first ultrasonic sensor 250. While the adhesive pad enables contact between the adhesive pad/drapes and the ultrasonic transducer, the adhesive pad may not facilitate a perfect, consistent contact along the entire length of the front face of the ultrasonic sensor. Rather, some small gaps may be present. Second view 501 includes a magnified view of one of these gaps, gap 508. It should be appreciated that while gaps may be present between the adhesive pad/drapes and the front face of the ultrasonic transducer, these gaps, such as gap 508, may be relatively small (e.g., gap 508 may have a length that is 1-10% of the length of gap 504) and may not extend along the entire front face of the ultrasonic sensor. Thus the presence of these gaps may not disrupt the ability of the ultrasonic sensor to emit pulses of ultrasonic signals or receive reflected ultrasonic signals.

Figure 4:
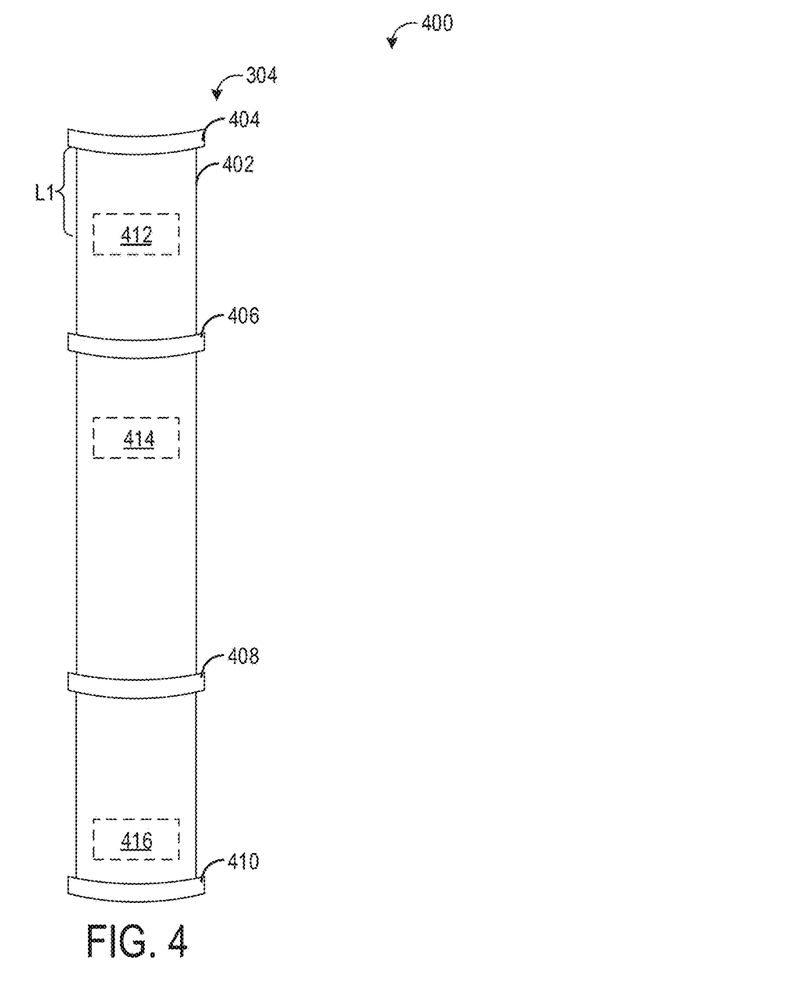
FIG. 4 shows an example sterile drape including adhesive pads.

FIG. 4 shows a view 400 of the second drape 304 in an unattached state, where the second drape 304 is not positioned around the C-arm of the x-ray imaging system. The second drape 304 includes a draping material 402, which may be comprised of plastic film, paper, plastic-backed paper, metal foil, or another suitable material. The draping material 402 may be substantially rectangular shaped and may be sized to cover the inner circumference of the C-arm, the outer sides of the C-arm, and/or at least some of the outer circumference of the C-arm. To hold the draping material in positon around the C-arm, the second drape 304 includes a plurality of clips, including a first clip 404, a second clip 406, a third clip 408, and a fourth clip 410. Each of the plurality of clips may be pre-coupled to the draping material 402. In other examples, each of the plurality of clips may be separate from the draping material 402 and may be coupled to the draping material at the time of the attachment of the second drape to the C-arm. Each clip may be shaped to wrap around the inner circumference of the C-arm, and may include biasing portions or another mechanism to engage the C-arm and hold the second drape 304 in position. It should be appreciated that the clips described herein are exemplary, and that other mechanisms for maintaining the second drape over and/or around the C-arm are possible, such as rubber bands, sliding rails, etc.

The draping material 402 includes one or more adhesive pads positioned on an inner surface of the draping material 402. The inner surface of the draping material is opposite a sterile outer surface of the draping material that is configured to face away from and overlie the component of the mobile medical imaging system (e.g., the C-arm) when the draping material is positioned over and/or around the component of the medical-ray imaging system. As shown, the draping material 402 includes three adhesive pads, a first adhesive pad 412, a second adhesive pad 414, and a third adhesive pad 416. Each adhesive pad may be positioned along draping material 402 at a respective position that corresponds to a location of a respective ultrasonic sensor on the C-arm. For example, the first adhesive pad 412 may be positioned relatively close to the top of the draping material 402 at a length L1 from the top edge of the draping material that matches or is within a threshold distance of the length L1 of the C-arm from a position where the second drape 304 is configured to terminate when positioned on the C-arm (e.g., near the detector) to the third ultrasonic sensor 254 (the length L1 on the C-arm is shown in FIG. 2).

Each adhesive pad may include a layer of adhesive material, such as pressure sensitive adhesive or vinyl film (which may have relatively high static cling), optionally covered in a backing layer that may be removed prior to adhering the adhesive pad on the ultrasonic sensor. Each adhesive pad may be larger than the dimensions of the front face/transducer of the ultrasonic sensor, to allow tolerance and ensure the front face of the ultrasonic sensor is fully covered by the adhesive pad.

While three adhesive pads are shown in FIG. 4, the second drape may include more or fewer adhesive pads, which may be based on how many ultrasonic sensors are positioned on/within the component the drape is configured to cover. Further, the draping material may have any suitable size or shape based on the size and shape of the component of the mobile medical imaging system that the drape is configured to cover. For example, the first drape 302 shown in FIG. 3 may be shaped similar to a bag, with an opening across the top and a cavity formed at least by a first piece of draping material and a second piece of draping material. The first piece of draping material and second piece of draping material may include inner surfaces configured to face the x-ray detector, and one or more adhesive pads may be positioned on one or more of the inner surfaces. Further, to facilitate proper placement of the sterile drapes so that the adhesive pad(s) on the drapes align with the corresponding ultrasonic sensor(s), the sterile drapes described herein may include position labels (e.g., top, bottom, front, back, etc.).

FIG. 6 shows a method 600 for collision avoidance with an x-ray imaging system. Method 600 may be carried out according to instructions stored in non-transitory memory of a computing device, such as controller 150 of FIG. 1. While method 600 is described herein as being implemented with the systems and components of FIGS. 1-3, method 600 may be implemented with other systems and components without departing from the scope of this disclosure.

At 602, the ultrasonic sensor(s) of the x-ray imaging system may be tested to confirm that sterile drapes have been positioned properly over the x-ray imaging system. As explained above, the sterile drapes may be positioned over and/or around various components of the x-ray imaging system, such as an x-ray detector (e.g., detector 207), an x-ray source (e.g., x-ray source 205), and a movable arm supporting the x-ray detector and the x-ray source (e.g., the C-arm 210), in order to ensure a sterile environment for conducting a procedure on a patient. The ultrasonic sensors may include ultrasonic sensors on the movable arm, at/near the detector, and/or at/near the x-ray source, such as the ultrasonic sensors described above with respect to FIG. 2. To prevent interference in object detection and collision avoidance based on output from the ultrasonic sensor(s), the sterile drapes may include adhesive pads at locations that correspond to locations of the ultrasonic sensors. During installation of the sterile drapes prior to a procedure on a patient, a user may bring a respective adhesive pad into contact with the front face of each ultrasonic sensor, to ensure the ultrasonic sensors are able to detect objects and are not blocked by the drapes. However, if the drapes are not positioned properly, such as if an ultrasonic sensor is not in contact with an adhesive pad, or if the drapes bunch or otherwise include flaps of material in front of but not in contact with an ultrasonic sensor, blockage of one or more ultrasonic sensors may occur, which may confound object detection, cause unnecessary alerts to be issued, and/or cause other issues.

Thus, each ultrasonic sensor on the x-ray imaging system may be tested to ensure each ultrasonic sensor can provide output usable to detect objects and facilitate collision avoidance. To test each sensor, an operator/user of the x-ray imaging system may enter an input (e.g., via user interface 160) indicating that the sterile drapes have been installed and/or requesting that sensor testing being carried out. In response, each ultrasonic sensor may be activated to transmit a pulse of ultrasonic signals. If any ultrasonic sensor detects an object (e.g., within a predetermined distance of the ultrasonic sensors), it may be determined that the drapes are improperly positioned (as no objects should be in proximity to the ultrasonic sensors during the testing). For example, assuming the x-ray imaging system is in a nominal, no-collision configuration (e.g., in a parked position), detection of an object below a pre-determined threshold (which may be different for each sensor) may indicate that one or more of the drapes are not correctly positioned. In another example, instructions may be output (e.g., via a display device and/or a speaker system) instructing the user to position an object (e.g., a hand) in front of each ultrasonic sensor sequentially, as the ultrasonic sensors are activated to transmit pulses of ultrasonic signals. If each ultrasonic sensor detects the object and then stops detecting the object once the object is moved out of range of the ultrasonic sensor, the drapes may be determined to be positioned properly. However, if an ultrasonic sensor cannot detect that the object has been moved into and then out of range of the ultrasonic sensor (because the drapes are instead detected), the drapes may be determined to be improperly positioned. In still further examples, additionally or alternatively, the positioning of the drapes may be tested to ensure the drapes have been placed over the x-ray imaging system. For example, once the x-ray imaging system assumes that a medical procedure is underway (e.g., imaging by the mobile medical imaging system has been requested), the range of each ultrasonic sensor may be determined based on how far away objects can be detected. If the x-ray imaging system determines that a range of an ultrasonic sensor is longer than expected, the drapes may be determined to be improperly placed (e.g., not positioned on the x-ray imaging system at all), as proper positioning of the drapes (e.g., contact between the adhesive pads and the ultrasonic sensors) is expected to reduce a maximum range of the ultrasonic sensors relative to when no drapes/adhesive pads are present.

At 604, method 600 includes determining if the drapes have been positioned improperly, based on the test described above. If the drapes are determined to have been positioned improperly, method 600 proceeds to 606 to output a notification (e.g., on display device 165) indicating that the drapes are improperly placed. In some examples, the notification may include an indication of which ultrasonic sensor(s) are blocked by the drapes, which may facilitate user repositioning of the drapes.

If the drapes are determined to be properly placed (and, if performed, once the notification has been output at 606), method 600 proceeds to 608 to determine the current position of the movable arm (e.g., C-arm) and patient information. The current position of the movable arm may be based on user input commands instructing movement of the movable arm and/or based on the commands sent by the controller of the x-ray imaging system to move the movable arm. The patient information may include patient height and/or weight (as determined from user input and/or obtained from an electronic medical record). At 610, output from the ultrasonic sensor(s) and/or additional proximity sensors of the x-ray imaging system is received. Any objects within range of the ultrasonic sensors and/or additional proximity sensors may be detected based on the output of the ultrasonic sensors and/or additional proximity sensors.

At 612, a model may be generated that estimates the position and/or trajectory of the movable arm relative to one or more detected objects. The position and/or trajectory of the movable arm relative to one or more detected objects may be modeled based on the determined current position of the movable arm, the patient information, and the output from the sensors. For example, based on the patient information, an a priori model may be generated including an estimated envelope of the patient (e.g., relative to a table supporting the patient), and then the position of the table and/or patient may be adjusted based on the output from the sensors (as well as any other objects detected by the proximity sensors). The current position of the movable arm may be determined relative to the table, the patient (including the patient envelope), and/or any other detected objects. Further, past movement of the movable arm as well as current commands to move the movable arm may be used to determine a trajectory of the movable arm.

The ultrasonic sensors provide distance information to adjust and register the a priori model of the environment of the x-ray imaging system. It is assumed that the x-ray imaging system knows its own geometry, based on physical dimensions and sensors (encoders, potentiometers, etc.) linked to every motion drive. This includes both the gantry and the patient table. The a priori model is about the environment and the patient. The patient may be modeled as a cylinder on the table top, or the patient may be modeled based on anthropometrics (e.g., the human body is divided in three sections to model head, torso-abdomen, and legs, either in a conservative way based on $95^{th}$ or $99^{th}$ percentile data, or based on patient information: adult/child, male/female, sex/age/weight/height). Either method for modeling the patient in the a priori model provides an approximation and lacks information as simple as position of the patient on the table top. Thus, the distance information from ultrasonic sensors may be used to provide information to update the a priori model resulting in a more accurate representation. This model can evolve during the procedure as the gantry/ C-arm is oriented around the patient. Regardless of the model at a given time, the information provided by any given sensor may be used to prevent contact of any moving part with the patient, as explained below.

Figure 7:
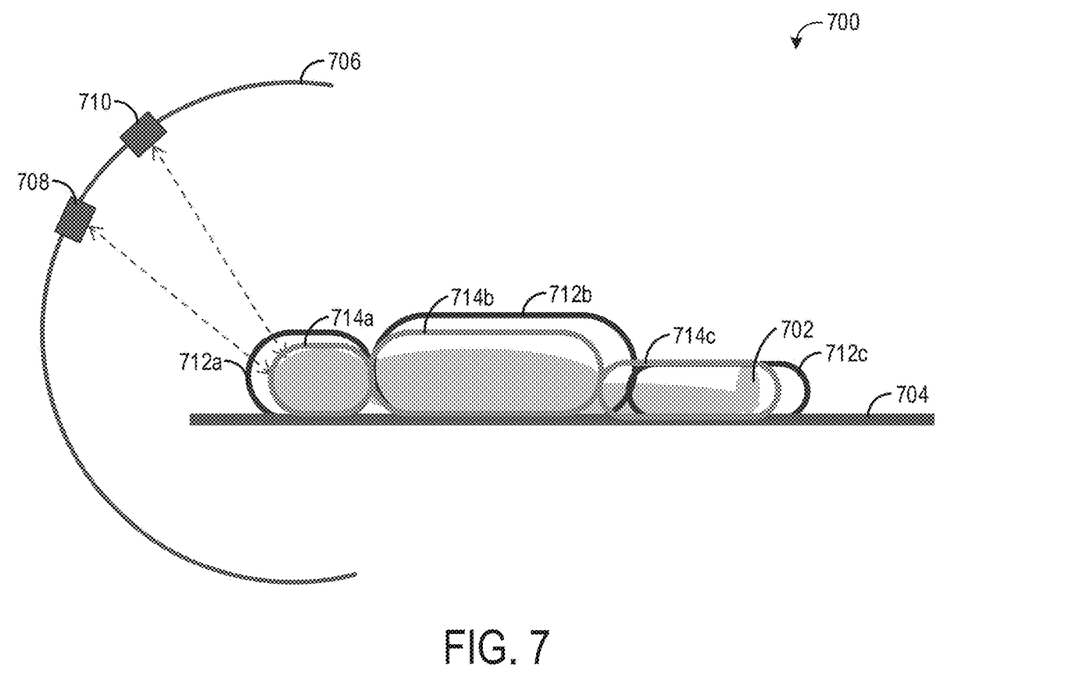
FIG. 7 schematically shows an example a priori model of a patient and adjustments to the model based on output from ultrasonic sensors of a movable arm of a medical imaging system in a first position.

FIG. 7 schematically shows an example 700 of an a priori model and adjustments to the model based on output from two ultrasonic sensors positioned on a movable arm (e.g., C-arm) of an x-ray imaging system, with the movable arm in a first position. In example 700, a patient 702 is shown positioned on a table 704. A movable arm 706 is in a first position relative to the patient. The movable arm 706 includes a first ultrasonic sensor 708 and a second ultrasonic sensor 710. In the first position, the ultrasonic sensors are positioned to receive distance information indicative of the size/shape/position of the patient's head.

The a priori model segments the patient's body into three segments. A first segment 712a estimates the size and position of the patient's head, a second segment 712b estimates the size and position of the patient's chest and abdomen, and a third segment 712c estimates the size and position of the patient's legs and feet. The segments of the a priori model may be estimated based on patient information (e.g., height, weight, age, etc.) as obtained from an electronic medical record and/or user input, at least in some examples.

Based on the distance information obtained by the ultrasonic sensors, the a priori model may be adjusted to register the model to the patient's actual size, shape, and position. A registered model is shown in FIG. 7. A first segment 714a of the registered model as shown in FIG. 7 is more closely aligned with the patient's head, due to the distance information indicative of the patient's head obtained from the ultrasonic sensors. A second segment 714b of the registered model and a third segment 714c of the registered model may each be adjusted relative to the a priori model, but due to the ultrasonic sensors being positioned closer to the patient's head, the second and third segments may still exhibit misalignment with the patient's actual chest/abdomen/legs.

Figure 8:
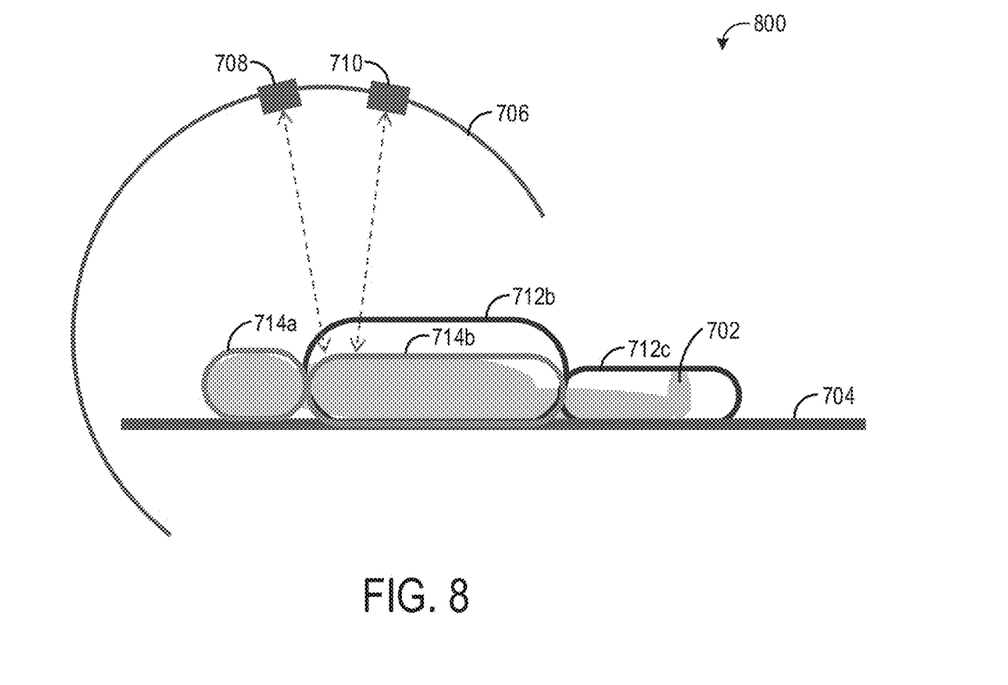
FIG. 8 schematically shows additional adjustments to the a priori model of FIG. 7 based on output from the ultrasonic sensors with the movable arm in a second position.

FIG. 8 shows a second example 800 of adjustments relative to the a priori model (resulting in further adjustments to the registered model) with the movable arm 706 in a second position. In the second position, the first ultrasonic sensor 708 and the second ultrasonic sensor 710 are moved to be above the patient's chest. As a result, additional distance information indicative of the positon, size, and/or shape of the patient's chest and abdomen is obtained. Thus, the second segment 714b of the registered model is more closely aligned/registered to the patient's actual chest and abdomen. As the movable arm is moved relative to the patient, additional distance information that is obtained from the ultrasonic sensors may be used to further update the model and register the model to the patient's actual size, shape, and position. The registered model may then be used to predict if a collision is about to occur between the patient and a component of the x-ray imaging system (e.g., the x-ray detector), and if so, a notification may be output to warn an operator of the x-ray imaging system of the potential collision.

Returning to FIG. 6, at 614, method 600 includes determining if the model indicates a potential collision between the movable arm (and/or the x-ray source or x-ray detector mounted to the movable arm) and an object, such as the patient, the table, medical staff, other medical equipment, etc. For example, based on the output from the proximity sensors (including the ultrasonic sensors) and/or the estimated patient envelope, an object in the medical environment (e.g., the patient) may be detected, with the position of the object relative to the current position of the movable arm determined. If the movable arm is moving or is commanded to move, and if the determined trajectory of the movable arm intersects with the detected object, the model may indicate a potential collision between the movable arm and the object.

If a potential collision is indicated, method 600 proceeds to 616 to output a notification indicating potential collision. The notification may be a visual notification that is displayed on a display device (e.g., display device 165) and/or the notification may be an audio notification output by a speaker (e.g., of the mobile medical imaging system). If a potential collision is not indicated (and upon outputting the notification indicating potential collision, when performed), method 600 proceeds to 618 to adjust the position of the movable arm when indicated. For example, an operator of the mobile medical imaging system may request the movable arm position be adjusted to position the x-ray source and x-ray detector in a desired position relative to the patient, to avoid a potential collision, move the movable arm out of the way of the patient to facilitate an event of the procedure being performed on the patient, etc. In response to the request to adjust the position of the movable arm, the movable arm may be moved.

At 620, imaging with the mobile medical imaging system is initiated when requested. For example, an operator (e.g., a clinician) may request imaging via a user input to the user interface of the mobile medical imaging system (e.g., user interface 160) or the user may request imaging via a user input to a toe-tap device or other user input device operably coupled to the mobile medical imaging system. Once imaging is requested, the x-ray source may be activated to emit a beam of x-ray radiation to the patient and the x-rays that pass through and around the patient may be received by the x-ray detector. The x-ray detector may be sampled and the sampled signals from the x-ray detectors may be used by the controller of the mobile medical imaging system to generate one or more images, which may be output for display on the display device. At 622, method 600 determines if any objects are within a threshold distance of the movable arm, based on the output from the proximity sensors. When the mobile medical imaging system is activated (e.g., moved out of a storage/resting position, powered on, etc.), the ultrasonic sensors may periodically (e.g., once a second, five times a second, or another suitable frequency) transmit pulses of ultrasonic signals and may detect any objects in range of the sensors based on whether the pulses of ultrasonic signals are reflected back to the sensors. Based on the amount of time from when a pulse is transmitted until a reflected ultrasonic signal is received at the ultrasonic sensor, a distance to an object may be determined. The threshold distance may be the range of the ultrasonic sensor/any detectable distance (such that if an object is detected, that object is within the threshold distance, regardless of how far from the movable arm the object is located). In other examples, the threshold distance may be a fraction of the range of the ultrasonic sensors, such as 5 cm, 10 cm, or another suitable distance. Further, any components of the x-ray imaging system that are in range of the ultrasonic sensor(s) and thus detected by the sensors may filtered out of the detection based on the known geometry and position of the components of the x-ray imaging system. For example, an ultrasonic sensor positioned on the C-arm of the x-ray imaging system may detect the x-ray detector once the x-ray detector has been moved to a given position to image a patient. The x-ray imaging system may know that the detected object is the x-ray detector based on knowing that the x-ray detector was commanded to move to the given position. In such an example, even though the ultrasonic sensor has detected an object within range, no notification is output, since the detected object is known to be a component of the x-ray imaging system.

If one or more objects are determined to be within the threshold distance from the movable arm/ultrasonic sensor (or detector, x-ray source, base of the x-ray imaging system, etc.), method 600 proceeds to 624 to output a notification indicating a potential collision, similar to the notification described above at 616. If no objects within the threshold distance are detected, method 600 proceeds to 626 to continue to adjust the model as the movable arm (and/or x-ray detector) position changes and/or object position(s) change. In this way, the model may continually be updated to reflect the current position of the movable arm and current position of any detectable objects, which may facilitate detection of potential collisions and subsequent output of notifications, as described above. Method 600 then returns.

It should be appreciated that the various events/determinations of method 600 described above could be performed in any order without departing from the scope of this disclosure. For example, imaging may commence at any time an operator requests imaging to be performed, regardless of whether proper placement of the drapes has been determined, the model has been generated, etc. Further, at any time the ultrasonic sensors and/or other proximity sensors detect an object within the threshold distance, a notification may be output. The movable arm position may be adjusted at any time the operator requests the movable arm be moved. However, in some examples, if a switch-based sensor is included in the x-ray imaging system and the switch-based sensor detects a collision (or if the ultrasonic/other proximity sensors indicate a collision has occurred), movement of the movable arm may be halted and may only commence once an updated user input requesting movement has been entered. Further, in addition to monitoring movement of the movable arm and notifying if a potential collision to about to occur with the moveable arm, the x-ray detector, x-ray source, base, etc., may each be monitored and if any potential collisions with these components is detected, a notification may be output.

While the above-described systems and methods have been described herein with respect to a ceiling-mounted C-arm x-ray imager, it is to be understood that the ultrasonic sensors, sterile draping including adhesive pads, collision model, etc., may be applied to other types of imaging systems, such as imaging systems with and without robotic arm, on wheels, ceiling suspended or floor mounted, and so forth, without departing from the scope of this disclosure.

A technical effect of including ultrasonic sensors on an x-ray imaging system is that multiple ultrasonic sensors may be included on the x-ray imaging system, increasing the accuracy and the robustness of the collision avoidance performed by the x-ray imaging system without greatly increasing costs of the x-ray imaging system. A technical effect of including adhesive pads on sterile draping configured to cover one or more components of the x-ray imaging system is that the adhesive pads may be used to prevent blockage of the ultrasonic sensors by the sterile draping, thereby facilitating usage of the ultrasonic sensors in collision avoidance of the x-ray imaging system.

An embodiment relates to an x-ray system, including a moveable arm comprising an x-ray source arranged at a first end and an x-ray detector arranged at a second end; an ultrasonic sensor positioned on the movable arm, the x-ray source, or the x-ray detector; and a sterile drape configured to be positioned over at least a portion of the movable arm, the x-ray source, and/or the x-ray detector, the sterile drape including an adhesive pad configured to contact a front face of the ultrasonic sensor. In a first example of the system, the ultrasonic sensor is a first ultrasonic sensor positioned on the x-ray detector, the adhesive pad is a first adhesive pad included in a first segment of the sterile drape, the first segment of the sterile drape configured to at least partially cover the x-ray detector, and the first adhesive pad is positioned on the first segment of the sterile drape at a location that corresponds to a location of the first ultrasonic sensor on the x-ray detector. In a second example of the system, which optionally includes the first example, the system further includes a second ultrasonic sensor positioned on the movable arm between the x-ray source and the x-ray detector and a second adhesive pad configured to contact a front face of the second ultrasonic sensor, the second adhesive pad positioned on a second segment of the sterile drape, the second segment configured to cover at least an inner circumference of the movable arm between the x-ray source and the x-ray detector and wherein the second adhesive pad is positioned on the second segment of the sterile drape at a location that corresponds to a location of the second ultrasonic sensor on the movable arm. In a third example of the system, which optionally includes one or both of the first and second examples, the system further includes a third ultrasonic sensor positioned at the x-ray source and a third adhesive pad configured to contact a front face of the third ultrasonic sensor, the third adhesive pad positioned on a third segment of the sterile drape, the third segment configured to at least partially cover the x-ray source. In a fourth example of the system, which optionally includes one or more or each of the first through third examples, the system further includes a controller storing instructions executable to determine a distance to an object based on output from the ultrasonic sensor, and if the distance is less than a threshold, output a first notification. In a fifth example of the system, which optionally includes one or more or each of the first through fourth examples, the instructions are executable to determine a predicted trajectory of the movable arm and a current position of the object relative to the movable arm, and if the predicted trajectory intersects the current position of the object, output a second notification. In a sixth example of the system, which optionally includes one or more or each of the first through fifth examples, the current position of the object is determined at least in part based on output from the ultrasonic sensor. In a seventh example of the system, which optionally includes one or more or each of the first through sixth examples, the adhesive pad includes a region of pressure-sensitive adhesive positioned on the sterile drape or a region of material having a higher static cling than adjacent regions of the sterile drape. In an eighth example of the system, which optionally includes one or more or each of the first through seventh examples, the system further includes an additional proximity sensor positioned on the movable arm, the x-ray source, or the x-ray detector, and wherein the sterile drape is separated from the additional proximity sensor by a gap. In a ninth example of the system, which optionally includes one or more or each of the first through eighth examples, the sterile drape lacks an adhesive pad at a location corresponding to a location of the additional proximity sensor.

An embodiment relates to a sterile draping system for an x-ray imaging system, the system including a draping material sized and shaped to cover a component of the x-ray imaging system, the draping material including a sterile outer surface configured to face away from and overlie the component of the x-ray imaging system when the draping material is positioned over and/or around the component of the x-ray imaging system; and an adhesive pad positioned on an inner surface of the draping material, the adhesive pad located on the inner surface at a position corresponding to a position of an ultrasonic sensor on the component of the x-ray imaging system, such that, when the draping material positioned over and/or around the component of the medical imaging system, the adhesive pad aligns with and is configured to be in face-sharing contact with a front face of the ultrasonic sensor. In a first example, the system further includes a fastening mechanism configured to maintain the draping material over and/or around the component of the x-ray imaging system. In a second example of the system, which optionally includes the first example, the draping material is a first draping material sized and shaped to cover a first component of the x-ray imaging system, and further comprising a second draping material sized and shaped to cover a second component of the x-ray imaging system and a third draping material sized and shaped to cover a third component of the x-ray imaging system. In a third example of the system, which optionally includes one or both of the first and second examples, the x-ray imaging system comprises a movable arm including an x-ray source arranged at a first end and an x-ray detector arranged at a second end, the first component comprises the x-ray detector, the second component comprises the x-ray source, and the third component comprises the movable arm between the x-ray source and the x-ray detector. In a fourth example of the system, which optionally includes one or more or each of the first through third examples, the system further includes a second adhesive pad positioned on an inner surface of the second draping material at a position corresponding to a position of a second ultrasonic sensor on the second component of the x-ray imaging system, such that, when the second draping material is positioned over and/or around the second component of the x-ray imaging system, the second adhesive pad aligns with and is configured to be in face-sharing contact with a front face of the second ultrasonic sensor. In a fifth example of the system, which optionally includes one or more or each of the first through fourth examples, the draping material lacks an adhesive pad at a location corresponding to a location of an additional sensor of the x-ray imaging system, such that, when the draping material is positioned over and/or around the component of the x-ray imaging system, a gap is present between the draping material and the additional sensor.

An embodiment provides a method for an x-ray imaging system, including determining, based on output from an ultrasonic sensor positioned on the x-ray imaging system, that a sterile draping system has been correctly positioned on the x-ray imaging system; upon determining that the sterile draping system has been correctly positioned, determining a distance between the ultrasonic sensor and an object based on output from the ultrasonic sensor; and if the distance is less than a threshold, outputting a notification. In a first example, the method further includes generating a model that includes a current position of a movable arm of the x-ray imaging system, an estimated trajectory of the movable arm, and a position of the object and/or one or more additional objects relative to the movable arm, the model generated in part based on output from the ultrasonic sensor. In a second example, which optionally includes the first example, the method further includes determining that a potential collision between the movable arm and the object and/or one or more additional objects could occur based on the model, and in response, outputting a second notification indicating the potential collision. In a third example of the method, which optionally includes one or both of the first and second examples, determining that the sterile draping has been correctly positioned comprises determining that an adhesive pad of the sterile draping has been placed in face-sharing contact with a front face of the ultrasonic sensor based on the output from the ultrasonic sensor.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An x-ray system, comprising:
a moveable arm comprising an x-ray source arranged at a first end and an x-ray detector arranged at a second end;
an ultrasonic sensor positioned on the movable arm, the x-ray source, or the x-ray detector; and
a sterile drape configured to be positioned over at least a portion of the movable arm, the x-ray source, and/or the x-ray detector, the sterile drape including an adhesive pad configured to contact a front face of the ultrasonic sensor the ultrasonic sensor is a first ultrasonic sensor positioned on the x-ray detector, wherein the adhesive pad is a first adhesive pad included in a first segment of the sterile drape, the first segment of the sterile drape configured to at least partially cover the x-ray detector, and wherein the first adhesive pad is positioned on the first segment of the sterile drape at a location that corresponds to a location of the first ultrasonic sensor on the x-ray detector, further comprising a second ultrasonic sensor positioned on the movable arm between the x-ray source and the x-ray detector and a second adhesive pad configured to contact a front face of the second ultrasonic sensor, the second adhesive pad positioned on a second segment of the sterile drape, the second segment configured to cover at least an inner circumference of the movable arm between the x-ray source and the x-ray detector and wherein the second adhesive pad is positioned on the second segment of the sterile drape at a location that corresponds to a location of the second ultrasonic sensor on the movable arm.

2. The system of claim 1, further comprising a third ultrasonic sensor positioned at the x-ray source and a third adhesive pad configured to contact a front face of the third ultrasonic sensor, the third adhesive pad positioned on a third segment of the sterile drape, the third segment configured to at least partially cover the x-ray source.

3. The system of claim 1, further comprising a controller storing instructions executable to determine a distance to an object based on output from the ultrasonic sensor, and if the distance is less than a threshold, output a first notification.

4. The system of claim 3, wherein the instructions are executable to determine a predicted trajectory of the movable arm and a current position of the object relative to the movable arm, and if the predicted trajectory intersects the current position of the object, output a second notification.

5. The system of claim 4, wherein the current position of the object is determined at least in part based on output from the ultrasonic sensor.

6. The system of claim 1, wherein the adhesive pad includes a region of pressure-sensitive adhesive positioned on the sterile drape or a region of material having a higher static cling than adjacent regions of the sterile drape.

7. The system of claim 1, further comprising an additional proximity sensor positioned on the movable arm, the x-ray source, or the x-ray detector, and wherein the sterile drape is separated from the additional proximity sensor by a gap.

8. The system of claim 7, wherein the sterile drape lacks an adhesive pad at a location corresponding to a location of the additional proximity sensor.

9. A method for an x-ray imaging system, comprising:
determining, based on output from an ultrasonic sensor positioned on the x-ray imaging system, that a sterile draping system has been correctly positioned on the x-ray imaging system;
upon determining that the sterile draping system has been correctly positioned, determining a distance between the ultrasonic sensor and an object based on output from the ultrasonic sensor; and
if the distance is less than a threshold, outputting a notification.

10. The method of claim 9, further comprising generating a model that includes a current position of a movable arm of the x-ray imaging system, an estimated trajectory of the movable arm, and a position of the object and/or one or more additional objects relative to the movable arm, the model generated in part based on output from the ultrasonic sensor.

11. The method of claim 10, further comprising determining that a potential collision between the movable arm and the object and/or one or more additional objects could occur based on the model, and in response, outputting a second notification indicating the potential collision.

12. The method of claim 9, wherein determining that the sterile draping has been correctly positioned comprises determining that an adhesive pad of the sterile draping has been placed in face-sharing contact with a front face of the ultrasonic sensor based on the output from the ultrasonic sensor.

* * * * *